(12) United States Patent
Fitzgerald et al.

(10) Patent No.: US 11,963,671 B2
(45) Date of Patent: Apr. 23, 2024

(54) CATHETER SYSTEM FOR INTRODUCING EXPANDABLE MEDICAL DEVICE AND METHODS OF USING SAME

(71) Applicant: TC1 LLC, St. Paul, MN (US)

(72) Inventors: Keif M. Fitzgerald, San Jose, CA (US); Mojan Kassayan, Atherton, CA (US); Ted Su, Sunnyvale, CA (US)

(73) Assignee: TC1 LLC, St. Paul, MN (US)

( * ) Notice: Subject to any disclaimer, the term of this patent is extended or adjusted under 35 U.S.C. 154(b) by 168 days.

(21) Appl. No.: 17/175,219

(22) Filed: Feb. 12, 2021

(65) Prior Publication Data

US 2022/0008053 A1   Jan. 13, 2022

Related U.S. Application Data

(60) Provisional application No. 62/705,662, filed on Jul. 9, 2020.

(51) Int. Cl.
*A61B 17/00* (2006.01)
*A61M 60/13* (2021.01)
(Continued)

(52) U.S. Cl.
CPC ....... *A61B 17/00234* (2013.01); *A61M 60/13* (2021.01); *A61M 60/135* (2021.01);
(Continued)

(58) Field of Classification Search
CPC .... A61B 17/00234; A61B 2017/00243; A61B 2017/00336; A61B 2017/0086;
(Continued)

(56) References Cited

U.S. PATENT DOCUMENTS 5,752,937 A * 5/1998 Otten ................ A61M 25/0668
604/161
8,864,811 B2   10/2014 Kao
(Continued)

FOREIGN PATENT DOCUMENTS

WO   WO-2015160990 A1 * 10/2015 .......... A61M 1/1008

OTHER PUBLICATIONS

International Search Report and Written Opinion for International Application No. PCT/US2021/040814, dated Jul. 8, 2021, 14 pages.
Written Opinion of The International Preliminary Examining Authority for International Application No. PCT/US2021/040814, dated Jul. 4, 2022, 5 pages.

*Primary Examiner* — Shaun L David
*Assistant Examiner* — Rachael L Geiger
(74) *Attorney, Agent, or Firm* — Armstrong Teasdale LLP

(57) ABSTRACT

A catheter system includes a catheter, a recovery sheath, and an outer sheath assembly. The catheter includes an elongate body having an expandable medical device coupled with a distal end thereof. The recovery sheath is disposed around a proximal section of the catheter body, and is sized and shaped to receive the expandable medical device therein. The recovery sheath is axially movable relative to the catheter body. The outer sheath assembly includes an outer sheath disposed over the catheter body. The outer sheath includes an elongate body that extends from a proximal end to a distal end, where the proximal end of the outer sheath body is positioned distally of the recovery sheath. The outer sheath includes a retention section sized and shaped to receive the expandable medical device therein and constrain the expandable medical device in a stored configuration. The outer sheath is removable from the catheter body.

18 Claims, 13 Drawing Sheets

(51) Int. Cl.
*A61M 60/135* (2021.01)
*A61M 60/216* (2021.01)

(52) U.S. Cl.
CPC . *A61M 60/216* (2021.01); *A61B 2017/00243* (2013.01); *A61B 2017/00336* (2013.01); *A61B 2017/00867* (2013.01); *A61M 2205/04* (2013.01)

(58) Field of Classification Search
CPC .. A61M 60/13; A61M 60/135; A61M 60/216; A61M 2205/04; A61M 60/237; A61M 60/865; A61M 2025/0681; A61M 25/0662
See application file for complete search history.

(56) References Cited

U.S. PATENT DOCUMENTS

| | | | |
|---|---|---|---|
| 10,215,187 | B2 | 2/2019 | McBride et al. |
| 2002/0099431 | A1 | 7/2002 | Armstrong et al. |
| 2003/0032941 | A1* | 2/2003 | Boyle ............... A61M 25/0668 604/533 |
| 2008/0208329 | A1 | 8/2008 | Bishop et al. |
| 2012/0296313 | A1 | 11/2012 | Andreacchi et al. |
| 2013/0085318 | A1* | 4/2013 | Toellner .............. A61M 60/414 600/16 |
| 2013/0217974 | A1* | 8/2013 | Levy .................. A61B 17/3421 600/210 |
| 2020/0390427 | A1* | 12/2020 | Eisenthal .......... A61B 10/0233 |

\* cited by examiner

CATHETER SYSTEM FOR INTRODUCING EXPANDABLE MEDICAL DEVICE AND METHODS OF USING SAME

CROSS-REFERENCE TO RELATED APPLICATION

This application claims priority to and the benefit of U.S. Provisional Patent Application No. 62/705,662, filed Jul. 9, 2020, entitled CATHETER SYSTEM FOR INTRODUCING EXPANDABLE MEDICAL DEVICE AND METHODS OF USING SAME, which is incorporated by reference herein in its entirety.

BACKGROUND OF THE DISCLOSURE a. Field of the Disclosure

The present disclosure relates generally to medical devices that are used in the human body. In particular, the present disclosure relates to a catheter system for introducing expandable medical devices into a mammalian body and methods of using the same.

b. Background

Heart disease is a major health problem that claims many lives per year. After a heart attack or other major cardiac event, a small number of patients can be treated with medicines or other non-invasive treatment. A significant number of other patients can recover from a heart attack or other cardiac event if provided with mechanical circulatory support in a timely manner.

In one conventional approach for treating patients, a blood pump is inserted into a heart chamber, such as into the left ventricle of the heart and the aortic arch, to assist the pumping function of the heart. Other known conventional applications involve providing for pumping venous blood from the right ventricle to the pulmonary artery for support of the right side of the heart. The object of the pump is to reduce the load on the heart muscle for a period of time allowing the affected heart muscle to recover and heal. Blood pumps may also be used in some cases for percutaneous coronary intervention. In some cases, surgical insertion may potentially cause additional stresses in heart failure patients.

When a catheter is inserted into the body of a patient, an introducer, typically formed of a thin walled polymeric tube, is placed through the site of the incision directly into the blood vessel. The catheter is then inserted (i.e., introduced) through the introducer into the blood vessel. After the catheter has been extended to its target location, the introducer may remain in place until the catheter is removed. In some instances, this can be several hours or even several days. In some catheter systems, the introducer may be removed from the catheter (e.g., by peeling away) and the patient's body after the catheter is advanced to the target location to reduce the cross-sectional area of the catheter system in the patient's vasculature. Other portions of the catheter system, however, remain in the patient's vasculature until the catheter is removed.

SUMMARY OF THE DISCLOSURE

The present disclosure is directed to a catheter system that includes a catheter, a recovery sheath, and an outer sheath assembly. The catheter includes an elongate body that has an expandable medical device coupled with a distal end thereof. The recovery sheath is disposed around a proximal section of the catheter body, and is sized and shaped to receive the expandable medical device therein in a stored configuration. The recovery sheath is axially movable relative to the catheter body. The outer sheath assembly includes an outer sheath disposed over the catheter body. The outer sheath includes an elongate body that extends from a proximal end to a distal end, where the proximal end of the outer sheath body is positioned distally of the recovery sheath. The outer sheath includes a retention section sized and shaped to receive the expandable medical device therein and constrain the expandable medical device in a stored configuration. The outer sheath is removable from the catheter body.

The present disclosure is further directed to a method that includes inserting an introducer sheath into a vasculature of a patient through an incision site, and introducing a catheter system into a proximal end of the introducer sheath and into the vasculature through the introducer sheath. The catheter system includes a catheter that includes an elongate body having an expandable medical device coupled with a distal end thereof. The catheter system also includes a recovery sheath disposed around a proximal section of the catheter body, and an outer sheath disposed around the catheter body and positioned distally from the recovery sheath. The method further includes removing the introducer sheath from the catheter system and the vasculature of the patient, and removing the outer sheath from the catheter body and the vasculature of the patient while the catheter body remains in the vasculature.

The present disclosure is further directed to a catheter system for a catheter pump. The system includes a catheter, a recovery sheath, and an outer sheath assembly. The catheter includes an elongate body having a distal portion including an expandable medical device including an expandable cannula and an impeller disposed within the expandable cannula and operable to draw fluid into the expandable cannula when rotated in the fluid. The catheter also includes a drive cable coupled to the impeller and disposed within a lumen defined by the catheter body. The recovery sheath is disposed around a proximal section of the catheter body, and is sized and shaped to receive the expandable medical device therein in a stored configuration. The recovery sheath is axially movable relative to the catheter body. The outer sheath assembly includes an outer sheath disposed over the catheter body. The outer sheath includes an elongate body extending from a proximal end to a distal end, where the proximal end of the outer sheath body is positioned distally of the recovery sheath. The outer sheath includes a retention section sized and shaped to receive the expandable medical device therein and constrain the expandable medical device in a stored configuration. The outer sheath is removable from the catheter body.

DETAILED DESCRIPTION OF THE DISCLOSURE

The present disclosure is directed to catheter systems for introducing expandable medical devices into a mammalian body that facilitate reducing obstructions or occlusions to blood flow while the catheter is positioned within the body. In particular, the catheter systems of the present disclosure enable one or more portions of the catheter system to be removed from the catheter body while the catheter is positioned within a patient to reduce the cross-sectional area of the catheter system within the patient's vasculature and thereby reduce obstructions to blood flow. For example, the catheter systems described herein include a removable outer sheath assembly that can be used to deliver an expandable medical device to a target site in a stored or collapsed configuration, and subsequently removed from the catheter system (e.g., by peeling away) and the patient's vasculature to reduce the cross-sectional area of the catheter system remaining the patient's vasculature.

Additionally, catheter systems of the present disclosure may include a recovery sheath assembly to facilitate sealing openings or gaps around the catheter body at the incision site following removal of the outer sheath assembly, and to facilitate re-sheathing and/or removing the expandable medical device when the catheter system is removed. For example, the recovery sheath assembly can include a removable plug configured to seal an opening at the incision site following removal of the outer sheath assembly. Consequently, catheter systems of the present disclosure may have a reduced-diameter proximal section, and thereby reduce obstructions to blood flow. Moreover, the recovery sheath assembly can include a relatively-large diameter recovery sheath that is held outside of a patient's body until the expandable medical device is ready to be removed from the patient's body. The recovery sheath can then be advanced into a patient's vasculature to facilitate collapsing and/or re-sheathing the expandable medical device within a lumen defined by the recovery sheath, and can be withdrawn from the patient's vasculature along with the collapsed medical device.

Figure 1:
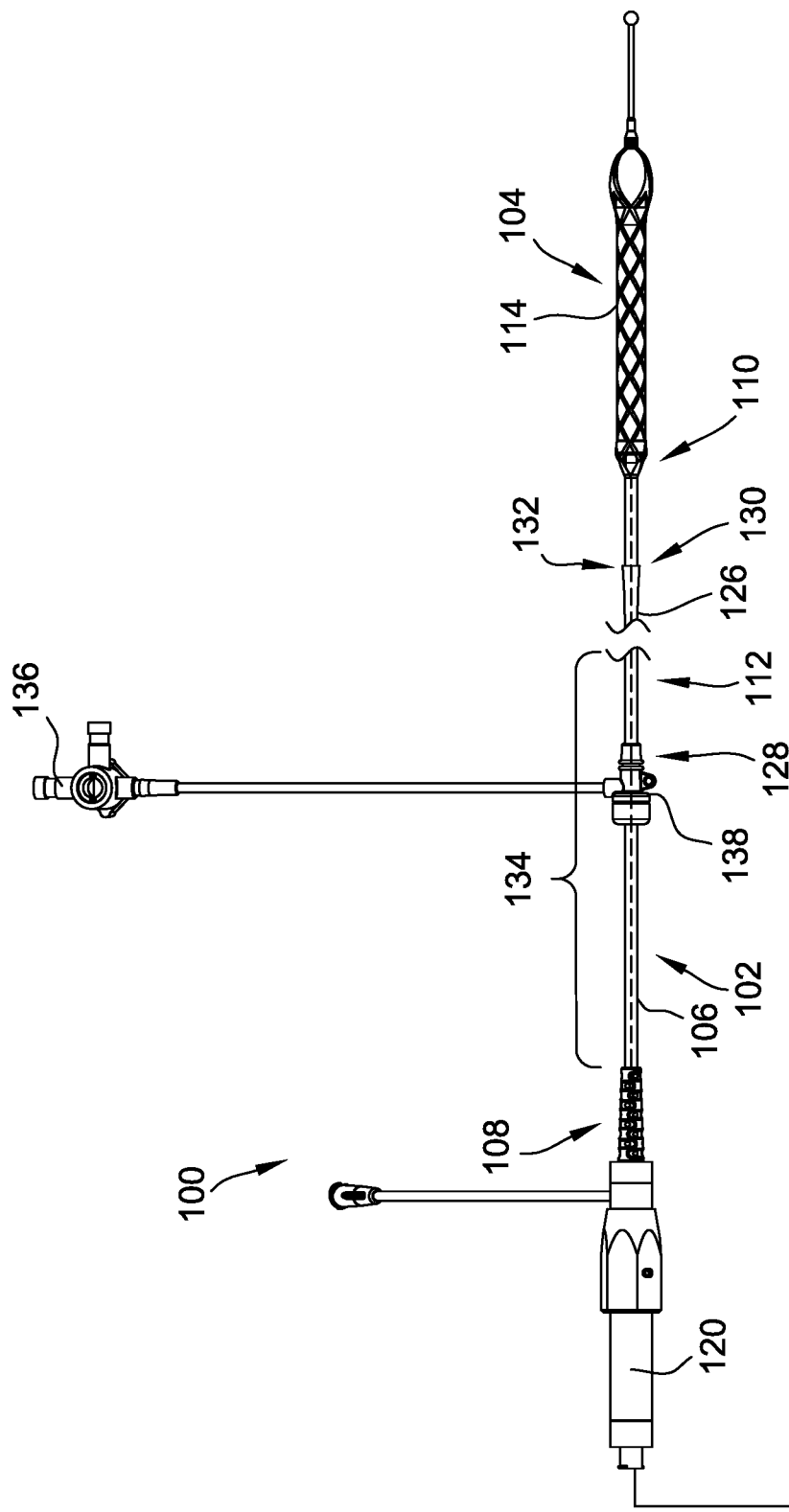
FIG. 1 is a plan view of a catheter system.
Figure 2:
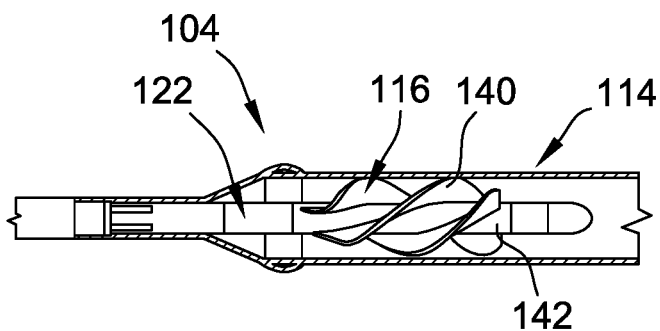
FIG. 2 is an enlarged sectional view of an expandable medical device of the catheter system shown in FIG. 1.
Figure 3:
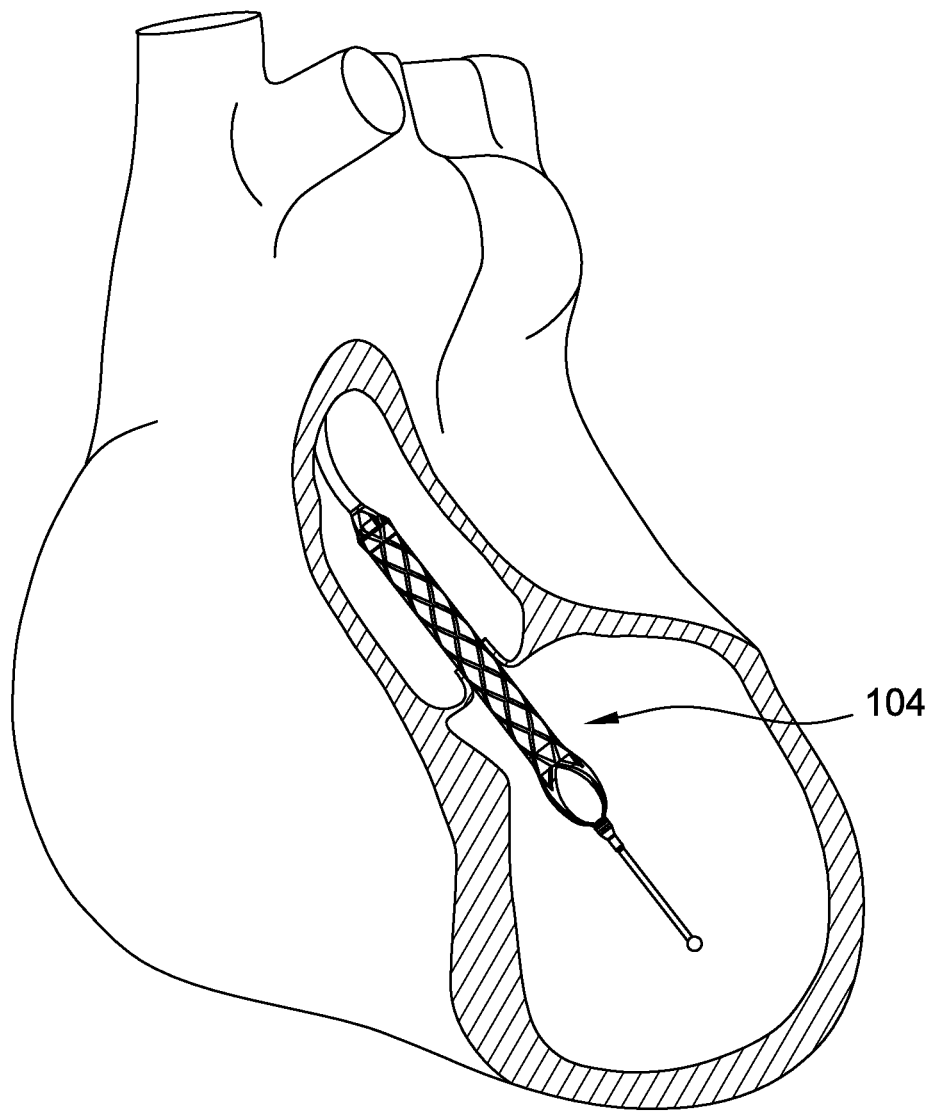
FIG. 3 illustrates one exemplary use of the catheter system shown in FIG. 1 within the chamber of a patient's heart.

Embodiments of the present disclosure are suitable for use in combination with numerous different catheters and catheter systems. FIGS. 1-3 illustrate one non-limiting example of a catheter system 100 in which embodiments of the present disclosure may be used. In this embodiment, the catheter system 100 is a percutaneous heart pump catheter suitable for providing high performance flow rates of blood within the left ventricle of a patient. While embodiments of the present disclosure are described with reference to a catheter pump, it should be understood that the disclosed embodiments are not limited to use with a catheter pump and may be used in combination with other catheters and catheter systems. Moreover, it should be understood that the disclosed embodiments are not limited to use with catheters, and may be used in combination with other surgical or medical devices, for example, to facilitate insertion, placement, and/or removal of such surgical and medical devices within a patient's body.

FIG. 1 is a plan view of the catheter system 100. As shown in FIG. 1, the catheter system 100 generally includes a catheter 102 and an expandable medical device 104. The catheter 102 has an elongate body 106 extending from a proximal end 108 to a distal end 110, and includes a retainer or outer sheath 112 disposed over the elongate body 106. As used herein, "proximal" refers to a direction away from the body of a patient and toward an operator of the catheter system 100. In contrast, "distal" as used herein refers to a direction toward the body of a patient and away from the operator. The expandable medical device 104 is coupled at the distal end 110 of the catheter body 106. As used herein, the term "expandable medical device" refers to a catheter medical device, typically coupled to the distal end of the catheter, that is radially expandable from a stored or delivery profile to a deployed or operational profile that is larger than the delivery profile. In this embodiment, the expandable medical device 104 is shown as a radially-expandable heart pump that includes a collapsible and expandable cannula 114 and a collapsible and expandable impeller 116 (shown in FIG. 2). It should be understood that the embodiments of the present disclosure are not limited to use with radially-expandable pumps, and are suitable for use with other types of expandable medical devices. In the collapsed state, the distal end of the catheter system 100 can be advanced to the heart, for example, through an artery. In the expanded state (shown in FIGS. 1-3), the medical device 104 is operational and is capable of performing one more functions for which it is designed. In the illustrated embodiment, the expandable medical device 104 is able to pump or output blood at high flow rates in the expanded state.

In the illustrated embodiment, the catheter system 100 is coupled with a motor 118 for driving the impeller 116. The catheter system 100 includes a coupling 120 that can be engaged with the motor 118 in certain embodiments. In various embodiments, the impeller 116 is rotated by the motor 118 via a drive cable or shaft 122 (FIG. 2) of the catheter 102 when the pump is operating. For example, the motor 118 can be disposed outside the patient. In some embodiments, the motor 118 is coupled to a controller 124 that directs operation of the motor and other components of the catheter system 100 (e.g., an infusion system). In some embodiments, the motor 118 is separate from the controller 124, e.g., to be placed closer to the patient. In other embodiments, the motor 118 is part of the controller 124. In still other embodiments, the motor is miniaturized to be insertable into the patient. In still other embodiments, the catheter system 100 may not include a motor 118.

The outer sheath 112 is disposed over the catheter body 106, and includes an elongate body 126 that extends from a proximal end 128 to a distal end 130. The elongate body 126 has at least one lumen defined therein that houses the elongate body 106 of the catheter 102. The catheter body 106 can be disposed in the lumen of the outer sheath body 126 such that the elongate bodies 106, 126 can move (e.g., axially) relative to one another. The outer sheath elongate body 126 is sized and shaped to receive the catheter body 106 therein to allow the catheter body 106 to be advanced through the at least one lumen defined by the outer sheath 112. In some embodiments, described further below, the outer sheath 112 is removable from the catheter body 106, for example, along one or more separation zones.

The outer sheath 112 is configured to maintain the expandable medical device 104 in the collapsed state to facilitate advancing the catheter 102 through a patient's vasculature. More specifically, the outer sheath 112 includes a retention section 132 located at the distal end 130 of the outer sheath elongate body 126 that is disposed over the expandable medical device 104 when in the collapsed state. The retention section 132 thereby enables the expandable medical device 104 to be maintained in the collapsed state until the catheter body distal end 110 is advanced to a desired position, for example, within a patient's heart. In some embodiments, the expandable medical device 104 is configured to self-deploy or self-expand into a deployed or expanded configuration when the expandable medical device 104 is advanced distally out of the outer sheath 112. The expandable medical device 104 can be collapsed into the collapsed state by advancing the outer sheath distal end 130 distally over the expandable medical device 104 to cause the expandable medical device 104 to collapse.

In some embodiments, the catheter 102 includes a reduced-diameter proximal portion or section 134 that has a smaller diameter than a distal end of the catheter 102. In the illustrated embodiment, for example, the retention section 132 of the outer sheath 112 has a suitable diameter for receiving and retaining the expandable medical device 104 therein. The expandable medical device 104, even in the collapsed state, may have a diameter larger than the remainder of the catheter body 106. That is, the catheter body distal end 110 and the expandable medical device 104, in the collapsed state, may have a larger diameter than a proximal section of the catheter 102 that extends from the catheter body proximal end 108. Accordingly, in some embodiments, such as the embodiment shown in FIG. 1, a proximal section 134 of the catheter 102 located at the proximal end 108 may have a reduced diameter relative to the distal end of the catheter 102. In some embodiments, for example, each of the catheter body 106 and the outer sheath 112 has a reduced diameter along the catheter proximal section 134 relative to the distal ends of the catheter body 106 and the outer sheath 112. In other embodiments, such as embodiments that do not have an outer sheath 112 or that include a removable outer sheath 112 (described in more detail below), only the catheter body 106 may have a reduced diameter along the catheter proximal section 134. The reduced-diameter proximal section 134 can have a diameter that is less than 95% of the diameter at the distal end of the catheter 102 (e.g., the diameter of the catheter body distal end 110 and/or the expandable medical device 104, in the collapsed state), less than 90% of the diameter at the distal end of the catheter 102, less than 85% of the diameter at the distal end of the catheter 102, less than 80% of the diameter at the distal end of the catheter 102, less than 75% of the diameter at the distal end of the catheter 102, less than 70% of the diameter at the distal end of the catheter 102, less than 60% of the diameter at the distal end of the catheter 102, and even less than 50% of the diameter at the distal end of the catheter 102. In some embodiments, for example, the distal end of the catheter 102 (i.e., the catheter body distal end 110 and/or the expandable medical device 104, in the collapsed state) has a diameter of between 13-16 French (Fr), and the reduced-diameter proximal section 134 (e.g., the catheter body 106) has a diameter of between 7-11 Fr. In one particular embodiment, the catheter body 106 has an outer diameter of 9 Fr along the reduced-diameter proximal section 134. Reducing the diameter of the catheter proximal section 134 facilitates lowering the profile of the portion of the catheter 102 in the body, and opens up space in the vasculature for blood flow around the remainder of the catheter system 100 that remains in the vasculature after the larger-diameter catheter distal end 110 and expandable medical device 104 are advanced therethrough.

In some embodiments, such as the embodiment illustrated in FIG. 1, a luer 136 or other suitable connector is connected in fluid communication with the catheter 102 and/or the outer sheath 112 at a corresponding proximal end thereof. In the illustrated embodiment, the luer 136 is connected by a hemostatic valve 138 configured to control fluid flow therethrough. The luer 136 can be configured to deliver fluids to the catheter 102, such as priming fluid, infusant, or any other suitable fluid.

With additional reference to FIG. 2, the expandable medical device 104 of the illustrated embodiment is a pump that includes a cannula 114 and an impeller 116. The cannula 114 has a stored, or collapsed configuration, and a deployed or expanded configuration. The cannula 114 can be formed of a superelastic material, and in some embodiments, may have various shape memory material properties. The impeller 116 is positioned within the cannula 114, and includes one or more blades 140 that extend from an impeller hub 142. In some embodiments, the blades 140 of the impeller 116 are self-expandable such that when the impeller 116 is positioned at a desired location, e.g., a chamber of a subject's heart, the blades 140 can be expanded into a deployed or expanded configuration, in which the blades 140 extend radially from the hub 142.

The cannula 114 and the impeller 116 may deploy from the stored configurations from within the outer sheath 112 into the expanded configuration. In such implementations, the outer sheath 112 can keep the blades 140 and the cannula 114 compressed until the blades 140 and cannula 114 are urged from within a lumen of the outer sheath 112. Once the blades 140 are released from the sheath assembly, the blades 140 can self-expand to a deployed configuration using strain energy stored in the blades 140 due to deformation of the blades 140 within the outer sheath 112. The expandable cannula 114 may also self-deploy using stored strain energy after being urged from the outer sheath 112. The combined energy stored in the expandable cannula 114 and blades 140 generates a force that preferably is opposed by the retention section 132 of the outer sheath 112. Thus, the retention section 132 should be of robust design to avoid premature deployment of the cannula 114 and blades 140, e.g., prior to positioning in the heart or other source of blood.

In the stored configuration, the expandable medical device 104 has a diameter that is preferably small enough to be inserted percutaneously into a patient's vascular system. Thus, it can be advantageous to fold the expandable medical device 104 into a small enough stored configuration such that the expandable medical device 104 can fit within the patient's veins or arteries, particularly small veins or arteries that are peripheral and superficial, e.g., femoral veins or arteries, jugular and subclavian veins, radial and subclavian arteries. In some embodiments, therefore, the expandable medical device 104 can have a diameter in the stored configuration corresponding to a catheter size between 8 Fr and 21 Fr.

When the expandable medical device 104 is positioned within a chamber of the heart, it can be advantageous to expand the expandable medical device 104 to have a diameter as large as possible in the expanded or deployed configuration. For example, in the illustrated embodiment, an increased diameter of the impeller 116 advantageously increases flow rate through the pump at a given rotational speed. A larger diameter impeller can also lead to an improved ratio of flow rate to hemolysis rate. In some implementations, the expandable medical device 104 can have a diameter corresponding to a catheter size greater than 12 Fr in the deployed configuration. In other embodiments, the expandable medical device 104 can have a diameter corresponding to a catheter size greater than 21 Fr in the deployed or expanded configuration.

FIG. 3 illustrates one exemplary use of the catheter system 100. In the illustrated embodiment, a distal portion of the catheter system 100, which includes the expandable medical device 104, is placed in the left ventricle (LV) of the heart to pump blood from the LV into the aorta. The catheter system 100 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the catheter system 100 in the heart is by percutaneous access and delivery using the Seldinger technique or other methods familiar to cardiologists. These approaches enable the catheter system 100 to be used in emergency medicine, a catheter lab and in other non-surgical settings.

Various additional aspects of the catheter system and associated components may be similar to those disclosed in U.S. Pat. Nos. 7,022,100; 7,393,181; 7,841,976; 7,998,054; 8,376,707; 8,485,961; 8,535,211; 8,591,393; 8,597,170; 8,721,517; 9,138,518; 9,358,329; 9,421,311; 9,446,179; 9,872,947; and 10,105,475, the entire contents of which are incorporated herein for all purposes by reference.

Figure 4:
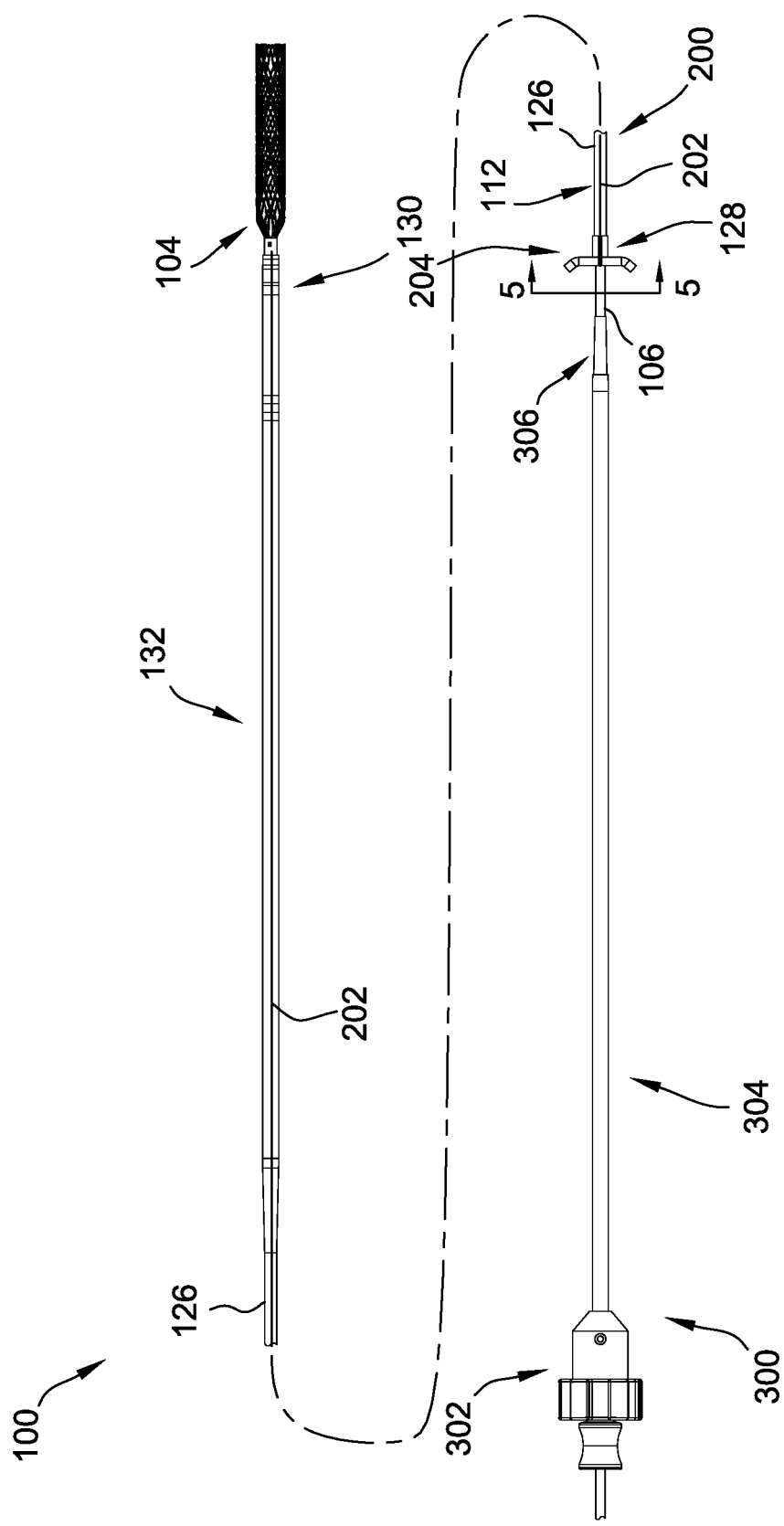
FIG. 4 is a plan view of the catheter system of FIG. 1 including a removable outer sheath assembly and a recovery sheath assembly.

FIG. 4 is another plan view of the catheter system 100 of FIG. 1 including a removable outer sheath assembly 200 and a recovery sheath assembly 300. The outer sheath assembly 200 and recovery sheath assembly 300 facilitate reducing the cross-sectional area or profile of the catheter system 100 that remains in a patient's body during operation. As described further herein, for example, at least a portion of the outer sheath assembly 200 is removable from the catheter body 106 to reduce the cross-sectional area or profile of the catheter system 100 within the patient's body, and the recovery sheath assembly 300 facilitates sealing or occluding openings or gaps formed between the catheter 102 and the incision site as a result of the reduced profile and further removing the expandable medical device 104 from the patient's body when the catheter system 100 is removed.

The outer sheath assembly 200 includes the outer sheath 112, which, in this embodiment, is removable from the patient's body and, in some embodiments, entirely from the catheter body 106 to lower the profile of the portion of the catheter system 100 that remains in the body. More specifically, at least a portion of the sheath assembly 200 is configured to separate from the catheter body 106 in a controlled manner at a selected time. In the illustrated embodiment, for example, a separation zone 202 is provided along the outer sheath body 126 to enable the outer sheath body 126 to be opened such that the catheter body 106 can pass through the separation zone 202. In some embodiments, the separation zone 202 enables the outer sheath body 126 to be separated into a plurality of pieces or segments.

The separation zone 202 may extend any suitable length along the outer sheath body 126 that enables the outer sheath assembly 200 to function as described herein. In the illustrated embodiment, the separation zone 202 extends the entire length of the outer sheath body 126, i.e., from the proximal end 128 of the outer sheath body 126 to the distal end 130 of the outer sheath body 126. In other embodiments, the separation zone 202 may extend less than the full length of the outer sheath body 126. In some embodiments, for example, the separation zone 202 extends distally from the proximal end 128 of the outer sheath body 126 towards the distal end 130 of the outer sheath body 126 and terminates proximally from the distal end 130 of the outer sheath body 126. In yet other embodiments, the separation zone 202 extends proximally from the distal end 130 of the outer sheath body 126 towards the proximal end 128 of the outer sheath body 126 and terminates distally from the proximal end 128 of the outer sheath body 126. In embodiments where the separation zone 202 extends less than the full length of the outer sheath body 126, a portion of the outer sheath 112 may remain on the catheter body 106 after another portion of the outer sheath 112 is removed via the separation zone 202. The portion of the outer sheath 112 that remains on the catheter body 106 may be removed from the patient's body through a lumen defined in the recovery sheath assembly 300, described in more detail below.

The separation zone or zones 202 can have any suitable configuration that facilities separating the outer sheath body 126 into a plurality of pieces or that facilitates changing the configuration of the outer sheath body 126 from a tubular body to one or more sheet-like bodies. In some embodiments, the separation zone 202 comprises a linear seam disposed along the outer sheath body 126. The separation zone 202 comprises two seams in one embodiment, one of the seams disposed along a first lateral side of the outer sheath body 126 and another of the seams disposed along a second later side of the outer sheath body 126. Two of a plurality of seams can be disposed at 180 degrees apart from each other on the outer sheath body 126. The linear seam or seams may include one or more lines of weakness, including, for example and without limitation, perforated lines, score lines, and combinations thereof. In one particular embodiment, the linear seam or seams are formed by laser cutting. In some embodiments, the linear seam or seams comprise a composite seam. For example, the composite seam can include a first portion adjacent the proximal end of the seam that has a resistance to separation (i.e., higher or lower) than a second portion of the composite seam adjacent the distal end of the seam.

In some embodiments, the separation zone or zones 202 may be formed in only a portion of the outer sheath body 126. For example, the outer sheath body 126 may comprise a reinforced structure including an inner tube and an outer jacket enclosing or covering the inner tube. In such embodiments, the separation zone or zones 202 may be formed in only a portion of the reinforced outer sheath body 126, such as along the inner tube. In one particular embodiment, the outer sheath body 126 comprises an inner tube and an outer polymeric jacket, wherein at least one separation zone 202 is formed along the inner tube, for example, by laser cutting (e.g., a laser cut perforation line). In such embodiments, the outer polymeric jacket may be free of separation zones.

Figure 5:
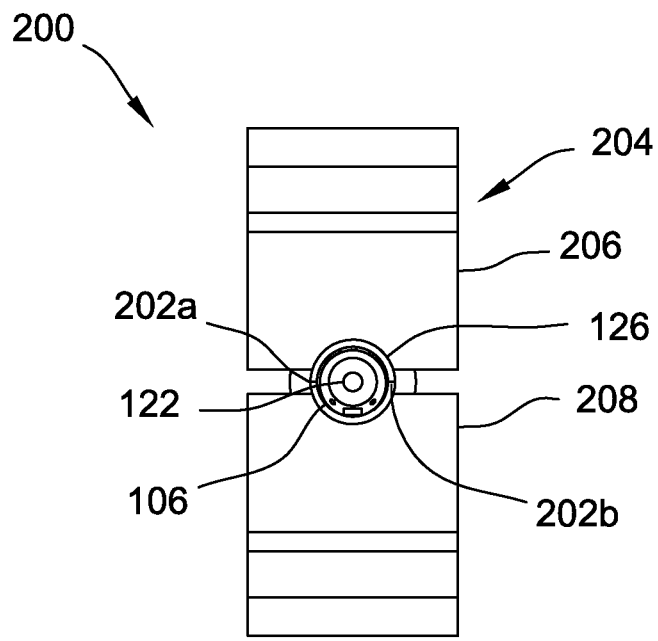
FIG. 5 is a sectional view of the catheter system of FIG. 4, taken along line "5-5" in FIG. 4.
Figure 6:
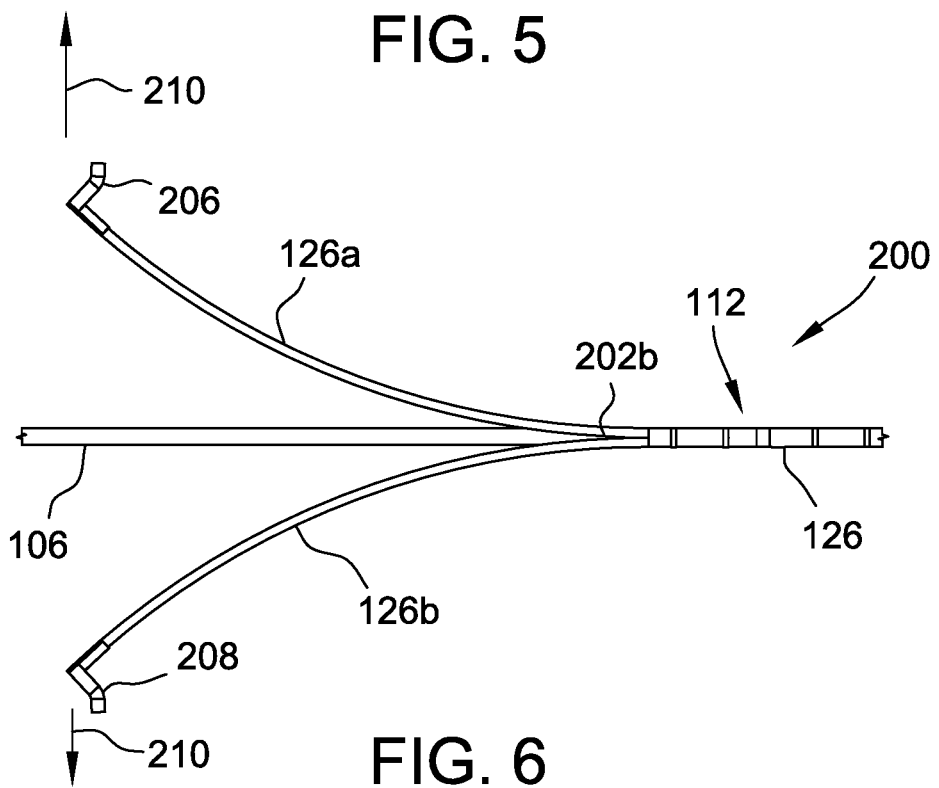
FIG. 6 is a side view of a portion of the catheter system of FIG. 4, illustrating the outer sheath assembly being removed from the catheter system.

With additional reference to FIGS. 5 and 6, the outer sheath assembly 200 of the illustrated embodiment includes a first lateral separation zone 202a disposed on a first lateral side of the outer sheath body 126, and a second lateral separation zone 202b disposed on a second lateral side of the outer sheath body 126. The first and second lateral sides can oppose each other, e.g., by being about 180 degrees apart. In the illustrated embodiment, the first and second lateral separation zones 202a, 202b are positioned diametrically opposite one another.

In some embodiments, the outer sheath assembly 200 may also include a hub to facilitate manipulating the outer sheath assembly 200 and/or removing the outer sheath assembly 200 from the catheter body 106. In the illustrated embodiment, for example, the outer sheath assembly 200 includes a hub 204 disposed at the proximal end 128 of the outer sheath body 126. As shown in FIGS. 5 and 6, the hub 204 includes first and second lateral handles 206, 208 that can be grasped by a clinician to provide relative movement between outer sheath body 126 and catheter body 106. The first and second handles 206, 208 can also be used to cause the hub 204 to separate into two pieces, and propagate separation of the outer sheath body 126 along the separation zone 202, for example, by applying laterally opposing forces (indicated by arrows 210) to the first and second handles 206, 208.

Figure 7:
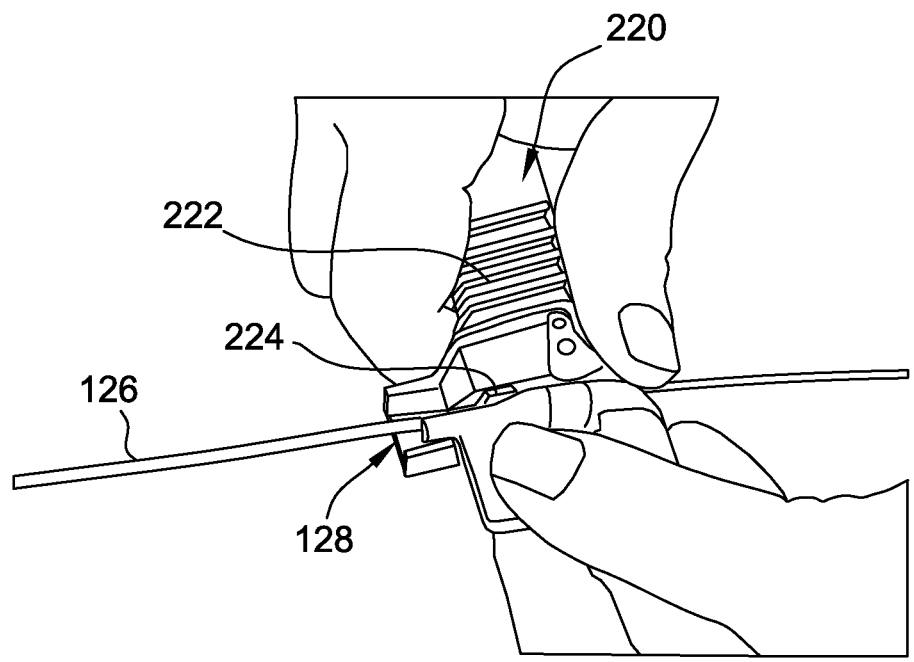
FIG. 7 is a perspective view of a cutting tool used to separate the outer sheath assembly along a separation zone.
Figure 8:
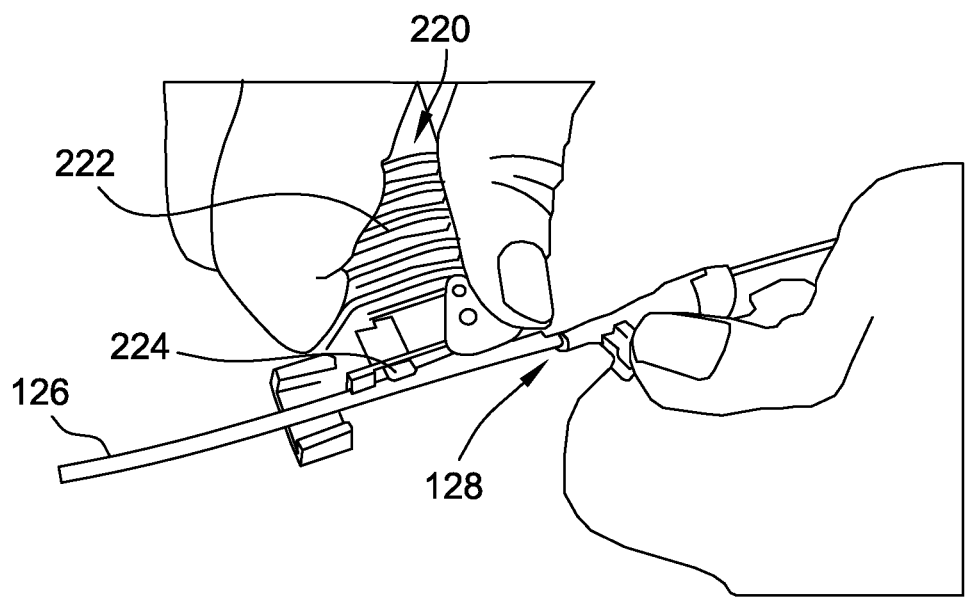
FIG. 8 is another perspective view of the cutting tool of FIG. 7 illustrating the outer sheath assembly being pulled proximally relative to the cutting tool to separate the outer sheath assembly along the separation zone.

In some embodiments, the catheter system 100 may further include a cutting tool 220, shown in FIGS. 7 and 8, to facilitate removing the outer sheath 112 from the catheter body 106. The cutting tool 220 may include, for example, a handle 222 and a blade 224 protruding from the handle 222 to facilitate cutting the outer sheath body 126 along one or more separation zones. In this embodiment, the separation zones may be pre-formed on the outer sheath body 126, or the cutting tool 220 may be used to form one or more separation zones along which the outer sheath body 126 is separated. In the embodiment illustrated in FIGS. 7 and 8, the cutting tool 220 is used to initiate a separation zone at the proximal end 128 of the outer sheath body 126. The outer sheath body 126 is pulled proximally relative to the cutting tool 220 while the blade 224 is engaged with the outer sheath body 126 to separate the outer sheath body 126 along the separation zone.

As described further herein, the outer sheath assembly 200 can be used to deliver the expandable medical device 104 to a target site within a patient's body while the outer sheath assembly 200 is in a first, intact configuration (shown in FIGS. 4 and 5). The outer sheath assembly 200 can subsequently be removed from the catheter body 106 and the patient's body by separating the outer sheath assembly 200 (e.g., along the separation zone 202, as illustrated in FIG. 6). In the illustrated embodiment, the outer sheath body 126 is separated into at least two portions or segments 126a, 126b, although in other embodiments the outer sheath body 126 may not be separated into multiple segments.

The recovery sheath assembly 300 is adapted to seal or occlude openings or gaps at the incision site following removal of the outer sheath assembly 200 from the catheter, and is further configured to facilitate removal of the expandable medical device 104 from the patient's body when the catheter system 100 is removed. The recovery sheath assembly 300 may have any suitable configuration that enables the catheter system 100 to function as described herein. In some embodiments, the recovery sheath assembly 300 has the same or similar configuration as the introducer sheath assembly described in U.S. patent application Ser. No. 16/864,545, filed May 1, 2020, the entire contents of which are incorporated herein by reference for all purposes.

Figure 9:
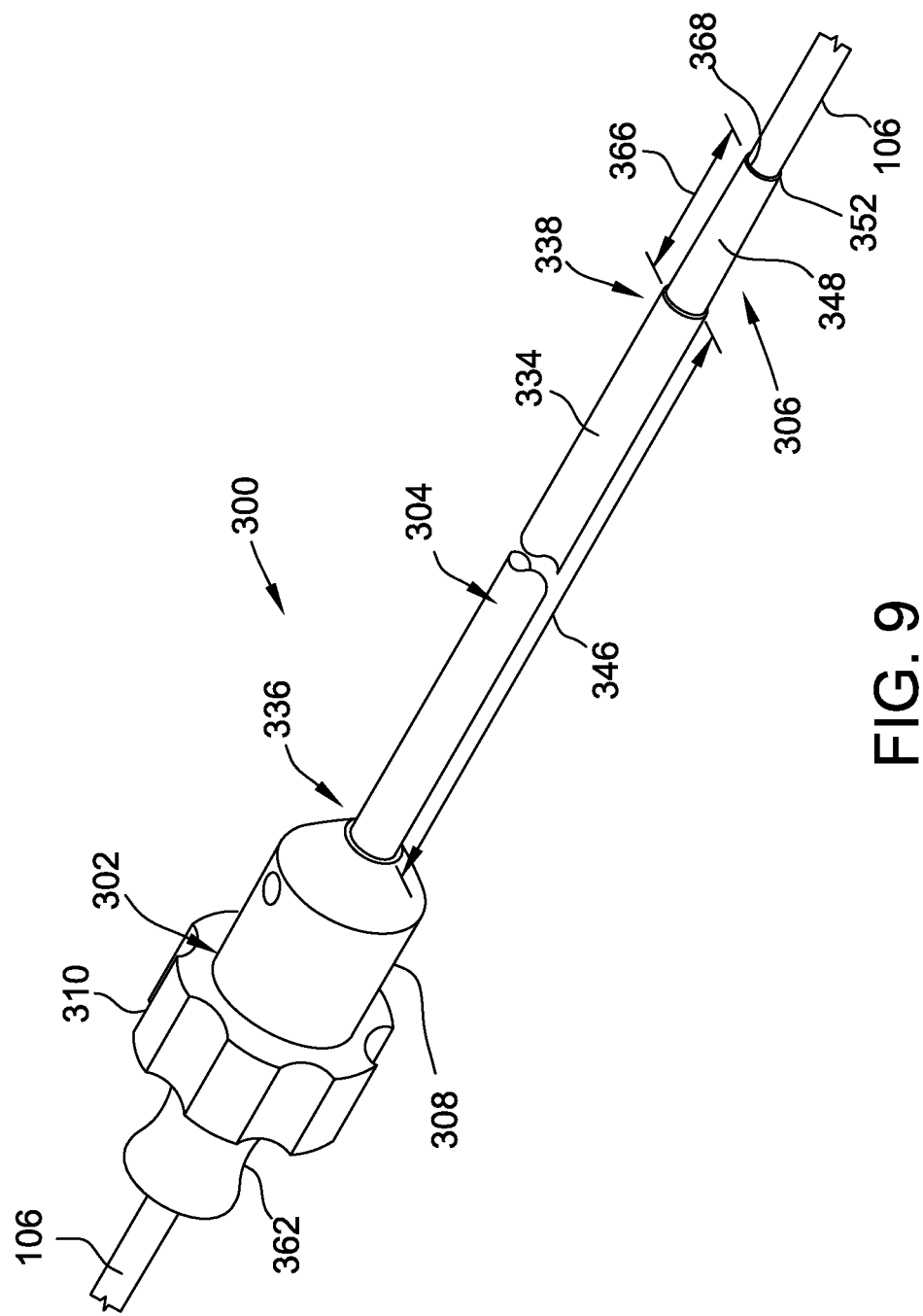
FIG. 9 is a perspective view of the recovery sheath assembly shown in FIG. 4.

With additional reference to FIG. 9, the recovery sheath assembly 300 of the illustrated embodiment includes a valve 302, a recovery sheath 304 connected to and protruding from the valve 302, and a tubular plug 306 that is releasably fixed relative to the recovery sheath 304 such that the plug can be removed or withdrawn from the recovery sheath 304, as described in greater detail herein. In this embodiment, the recovery sheath 304 and the tubular plug 306 are coupled to the valve 302 such that the recovery sheath assembly 300 is movable as a unit along the catheter body 106.

Figure 10:
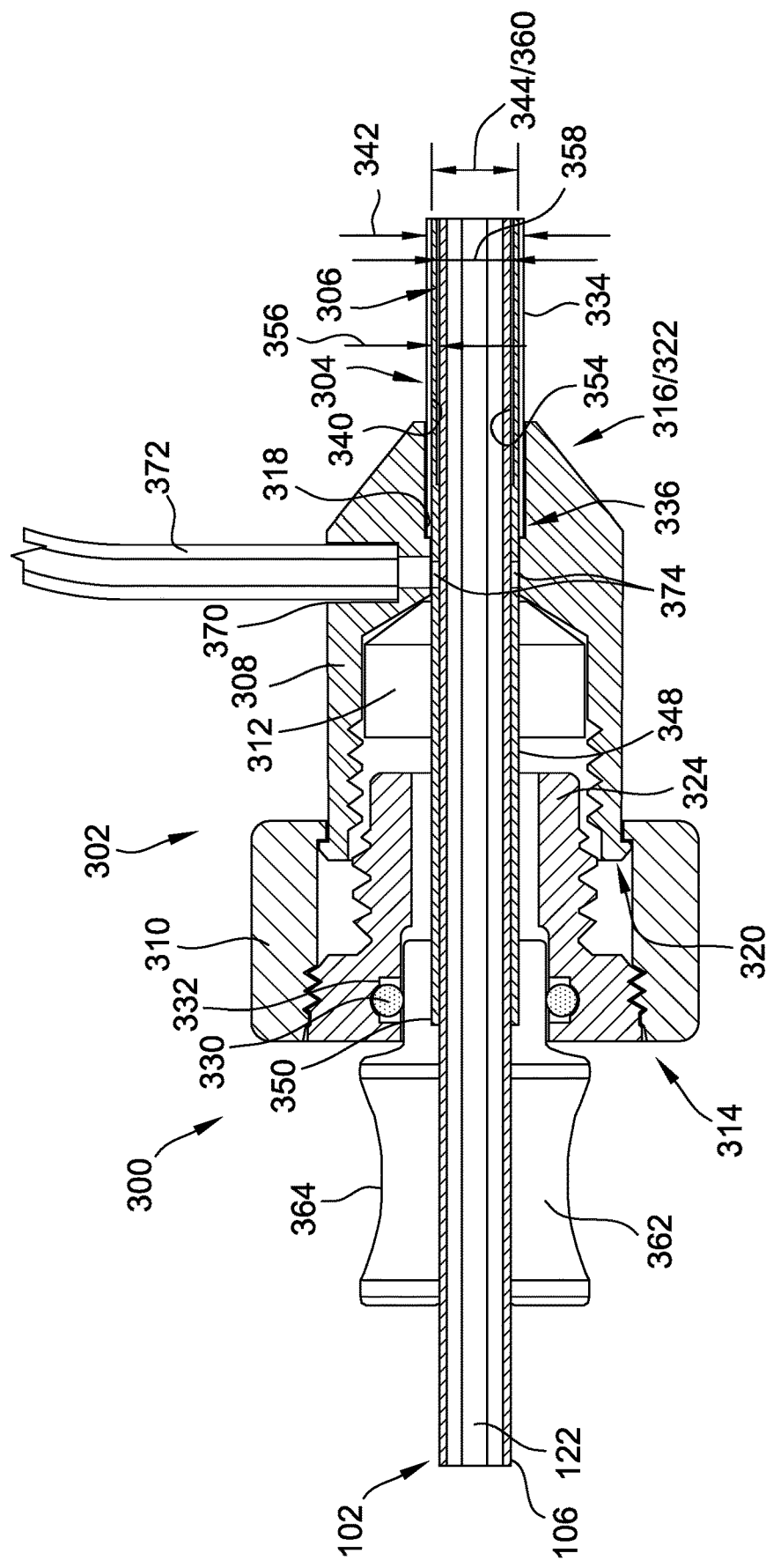
FIG. 10 is a sectional view of the recovery sheath assembly shown in FIG. 4.

With additional reference to FIG. 10, the recovery sheath assembly 300 is disposed on the catheter 102, specifically, around the catheter body 106. In the illustrated embodiment, the recovery sheath assembly 300 is disposed on a proximal end of the catheter 102, specifically, along the reduced-diameter proximal section 134 (shown in FIG. 1) of the catheter 102. In some embodiments, the recovery sheath assembly 300 is disposed on the catheter 102 distally from the fluid valve 138 (shown in FIG. 1). In other embodiments, the fluid valve 138 may be incorporated with the recovery sheath assembly 300, for example, as the valve 302.

The valve 302 is configured to control fluid flow through one or more lumens defined by the recovery sheath assembly 300 and/or the catheter 102, for example, to inhibit blood flow out of a patient. The valve 302 includes a valve body 308, an actuator 310, and a valve member 312. The valve 302 has a proximal end 314 and a distal end 316, and has an elongate passage 318 defined therein. In this embodiment, the elongate passage 318 is defined by and extends through each of the valve body 308, the actuator 310, and the valve member 312. The valve body 308 has a proximal end 320 and a distal end 322, which in this embodiment, defines the distal end 316 of the valve 302. The actuator 310 is coupled to the valve body proximal end 320, and the valve member 312 is positioned between the valve body 308 and the actuator 310.

In this embodiment, the valve 302 is a rotatable hemostatic valve that includes a rotatable actuator 310 and a compressible valve member 312. More specifically, the actuator 310 is configured to compress the valve member 312 between an engagement portion 324 of the actuator 310 and the valve body 308, and thereby cause the valve member 312 to deflect radially inward and apply a radial compressive force on the plug 306. The valve member 312 thereby seals one or more lumens defined between the plug 306 and the catheter 102 and/or defined within the catheter 102. The actuator 310 is threadably coupled to the valve body 308 in this embodiment such that rotation of the actuator 310 in a first direction (e.g., clockwise) displaces the actuator 310 towards the valve member 312, and compresses the valve member 312 between the actuator 310 and the valve body 308. Rotation of the actuator 310 in a second, opposite direction (e.g., counterclockwise) displaces the actuator 310 away from the valve member 312, releasing compression on the valve member 312. It should be understood that the recovery sheath assembly 300 may include any suitable valve that enables the recovery sheath assembly 300 to function as described herein, and is not limited to rotatable hemostatic valves.

The valve 302 also includes a retainer 330 for releasably fixing the plug 306 relative to the recovery sheath 304. In this embodiment, the retainer 330 includes an O-ring that is positioned within an annular recess 332 defined by the actuator 310. The O-ring engages a portion of the plug 306, and maintains an axial position of the plug 306 relative to the recovery sheath 304 via a friction fit. In other embodiments, the valve 302 may include a retainer other than an O-ring for releasably fixing the plug 306 relative to the recovery sheath 304. In yet other embodiments, one or both of the plug 306 and the recovery sheath 304 may include a retainer for maintaining a fixed relative position of the two components.

The recovery sheath 304 includes an elongate body 334 extending from a proximal end 336 to a distal end 338, and defines a lumen 340 therein that extends from the recovery sheath proximal end 336 to the recovery sheath distal end 338. The recovery sheath body 334 has an outer diameter 342 that is sized and shaped to seal an incision formed, for example, in a patient's vasculature. The recovery sheath body 334 may have any suitable outer diameter 342 that enables the recovery sheath assembly 300 to function as described herein. In some embodiments, the outer diameter 342 of the recovery sheath 304 is the same as the introducer sheath used to introduce the catheter 102 into a patient's vasculature. Suitable outer diameters 342 of the recovery sheath body 334 include, for example and without limitation, between 8 Fr and 21 Fr, between 8 Fr and 19 Fr, between 10 Fr and 21 Fr, between 8 Fr and 17 Fr, between 10 Fr and 19 Fr, between 12 Fr and 21 Fr, between 8 Fr and 15 Fr, between 10 Fr and 17 Fr, between 12 Fr and 19 Fr, between 14 Fr and 21 Fr, between 10 Fr and 15 Fr, between 12 Fr and 17 Fr, between 14 Fr and 19 Fr, and between 13 Fr and 16 Fr. In some embodiments, the outer diameter 342 of the recovery sheath body 334 is less than 8 Fr. In yet other embodiments, the outer diameter 342 of the recovery sheath 304 is greater than 21 Fr. In one embodiment, the outer diameter 342 of the recovery sheath body 334 is 14 Fr.

The recovery sheath lumen 340 is configured to be slidably disposed over the catheter 102 (e.g., over the catheter body 106) such that the catheter 102 can be advanced distally and proximally relative to the recovery sheath 304. The recovery sheath lumen 340 is sized to permit the expandable medical device 104 and, in some embodiments, the outer sheath retention section 132 to fit therethrough. For example, the recovery sheath 304 has an inner diameter 344 sized larger than an outer diameter of the expandable medical device 104 in the collapsed state such that the recovery sheath 304 can be used to re-sheath or collapse the expandable medical device 104 when removing the catheter 102 from a patient. In some embodiments, the recovery sheath inner diameter 344 is sized to permit an object having an outer diameter of up to 13 Fr, up to 14 Fr, up to 15 Fr, and even up to 16 Fr to pass through the recovery sheath lumen 340.

In this embodiment, the recovery sheath 304 is coupled to the valve body 308 at the valve body distal end 322. The recovery sheath 304 may be coupled to the valve body 308 using any suitable fastening means including, for example and without limitation, a frictional fit, adhesives, and tacking. The recovery sheath 304 extends from the valve body distal end 322 a length 346 (FIG. 9). The recovery sheath 304 may extend from the valve body 308 by any suitable length 346 that enables the recovery sheath assembly 300 to function as described herein including, for example and without limitation, between 10 centimeters (cm) and 40 cm, between 10 cm and 35 cm, between 20 cm and 45 cm, between 10 cm and 30 cm, between 20 cm and 40 cm, between 25 cm and 40 cm, between 10 cm and 25 cm, between 25 cm and 35 cm, between 20 cm and 30 cm, between 30 cm and 40 cm, and between 10 cm and 20 cm. The length 346 the recovery sheath 304 extends from the valve body 308 is sufficient to allow the distal end 338 of the recovery sheath 304 to be inserted into a patient's vasculature to allow the expandable medical device 104 to be re-sheathed with the recovery sheath 304 while still in the patient's vasculature.

The recovery sheath 304 may be constructed of any suitable materials using any suitable techniques that enable the recovery sheath 304 to function as described herein. In some embodiments, the recovery sheath 304 has a suitably rigid construction to enable to the recovery sheath 304 to re-sheath or collapse the expandable medical device 104 when the catheter 102 is removed from a patient. Suitable constructions for the recovery sheath 304 include, for example and without limitation, a braided reinforced sheath (e.g., braided nitinol) with a lubricious liner, and a thicker-wall single material component.

The plug 306 is disposed along the catheter 102, between the recovery sheath 304 and the catheter 102. The plug includes an elongate tubular body 348 extending from a proximal end 350 (FIG. 10) to a distal end 352 of the plug 306, and defines a lumen 354 extending therethrough. The elongate body 348 extends through each of the elongate passage 318 and the recovery sheath lumen 340.

In some embodiments, such as the embodiment illustrated in FIGS. 4-8, the recovery sheath assembly 300 is disposed over the reduced-diameter proximal section 134 of the catheter 102 such that a gap 356 is defined between the recovery sheath 304 and the catheter 102 (e.g., the catheter body 106). As shown in FIG. 10, the plug 306 is disposed over the catheter 102 (specifically, over the catheter body 106), and between the catheter 102 and the recovery sheath 304 to occlude the gap 356 defined therebetween. The plug 306 has a suitable thickness to substantially fill or occlude the gap 356 and inhibit outward fluid flow (i.e., towards a proximal end of the recovery sheath assembly 300) therethrough. That is, in some embodiments, the plug body 348 has a suitable inner diameter 358 and outer diameter 360 to substantially fill the gap 356 between the recovery sheath 304 and the catheter 102. In some embodiments, for example, the plug body 348 has an outer diameter 360 of between 85% and 100% of the recovery sheath inner diameter 344, between 85% and 95% of the recovery sheath inner diameter 344, or between 90% and 100% of the recovery sheath inner diameter 344. Further, in some embodiments, the plug body 348 has an inner diameter 358 of between 1.0 and 1.25 times an outer diameter of the catheter 102 (e.g., the reduced-diameter proximal section of the catheter 102), between 1.0 and 1.2 times an outer diameter of the catheter 102, or between 1.0 and 1.15 times an outer diameter of the catheter 102. In one particular embodiment, the plug body 348 has an outer diameter 360 of 13 Fr, and an inner diameter 358 sized to permit an object having a diameter up to 10 Fr to pass therethrough.

As noted above, the plug 306 is releasably fixed relative to the recovery sheath 304 such that the plug 306 can be removed from the recovery sheath lumen 340, for example, to allow a relatively-large diameter distal end of the catheter 102 (e.g., the expandable medical device 104) to pass therethrough. In the illustrated embodiment, the plug 306 is releasably coupled to the valve 302, specifically, to the valve actuator 310 by an O-ring. In one method of using the recovery sheath assembly 300, the plug 306 is removed from the recovery sheath lumen 340 by pulling the plug 306 proximally relative to the recovery sheath 304, thereby decoupling the plug 306 from the valve 302, prior to the catheter 102 being removed from a patient's vasculature.

In the illustrated embodiment, the plug 306 includes a handle 362 coupled with the plug proximal end 350 to facilitate positioning and/or moving the plug 306 relative to the recovery sheath 304 and/or the valve 302. The handle 362 has a diameter larger than the plug body outer diameter 360 to facilitate grasping the handle 362. Further, in this embodiment, the handle 362 includes an annular concave groove 364 to facilitate grasping the handle 362. The handle 362 may include other gripping features in addition to or as an alternative to the concave groove, including, for example and without limitations, ribs, grooves, and textured surface(s). The handle 362 extends proximally from the valve proximal end 314, and is accessible from an exterior of the valve 302. The plug handle 362 may be formed integrally with the plug body 348 (i.e., as a unitary member), or may be formed separately from the plug body 348 and coupled thereto. In the illustrated embodiment, the plug 306 is fixed relative to the recovery sheath 304 by the plug handle 362 being secured to the O-ring via a frictional fit.

Referring again to FIG. 9, the plug distal end 352 protrudes from the distal end 338 of the recovery sheath 304 by a distance 366. The plug distal end 352 may protrude from the recovery sheath distal end 338 by any suitable distance 366 that enables the recovery sheath assembly 300 to function as described herein. In some embodiments, for example, the plug distal end 352 protrudes from the recovery sheath distal end 338 by a distance 366 of up to 1 cm, up to 2 cm, up to 3 cm, 4 cm, up to 5 cm, up to 6 cm, up to 7 cm, up to 8 cm, and even up to 10 cm.

In some embodiments, the plug distal end 352 tapers radially inward towards a distal tip 368 of the plug 306 to facilitate insertion of the plug distal end 352 into an incision site. Moreover, in some embodiments, the plug body 348 includes multiple hardness or durometer zones. That is, the plug body 348 may be constructed to have zones of differing hardness or stiffness. In some embodiments, for example, the plug distal end 352 has a relatively stiff or hard construction relative to the remainder of the plug body 348, for example, to facilitate insertion of the plug distal end 352 into an incision site. Additionally or alternatively, in some embodiments, a proximal portion of the plug body 348, such as the portion of the plug body 348 that engages the valve member 312, has a relatively soft, flexible, or elastic construction relative to the remainder of the plug body 348, for example, to facilitate compression by the valve member 312 and sealing of one or more lumens defined by the plug body 348 and/or the catheter 102. That is, the proximal portion of the plug body 348 may be radially compliant to facilitate sealing the lumens defined by or within the plug 306.

The plug 306 may be constructed of any suitable materials using any suitable techniques that enable the plug 306 to function as described herein. In one embodiment, the plug 306 is formed by an extrusion process, and multiple hardness zones are formed along the plug body 348 using known reflow techniques. Suitable materials from which the plug 306 may be constructed include, for example and without limitation, polyethylene.

Referring to FIG. 10, the valve body 308 defines a fluid port 370 that is in fluid communication with the valve body elongate passage 318. The fluid port 370 is configured for connection to a fluid source (e.g., heparinized saline) via a fluid line 372, and allows one or more fluids F to be delivered or supplied to one or more lumens defined by the recovery sheath 304 and/or the plug 306. In some embodiments, fluid is supplied to one or more lumens defined by the recovery sheath 304 and/or the plug 306 to flush the lumens and inhibit blood products from accumulating and forming clots within the recovery sheath assembly 300. In this embodiment, the fluid port 370 is located between the valve member 312 and the distal end 322 of the valve body 308, and extends radially inward from a radial outer surface of the valve body 308 to the elongate passage 318.

The recovery sheath proximal end 336 is positioned distally from the valve body fluid port 370 such that the recovery sheath lumen 340 is in fluid communication with the fluid port 370. Additionally, in this embodiment, the plug 306 defines one or more fluid ports 374 that extend through the plug body 348. When the plug 306 is connected to the valve 302, as shown in FIGS. 7 and 8, the plug fluid ports 374 are coupled in fluid communication with the valve body fluid port 370 such that fluid may be supplied to the plug lumen 354 via the valve body fluid port 370. In other words, the plug fluid ports 374 enable fluid to be supplied to the plug lumen 354 using the same fluid port 370 used to supply fluid to the recovery sheath lumen 340. In this embodiment, the plug fluid ports 374 are located distally from the elastic proximal portion of the plug body 348 that engages the valve member 312 to inhibit fluid supplied through the fluid port 370 from leaking out of the proximal end of the recovery sheath assembly 300.

Figure 11:
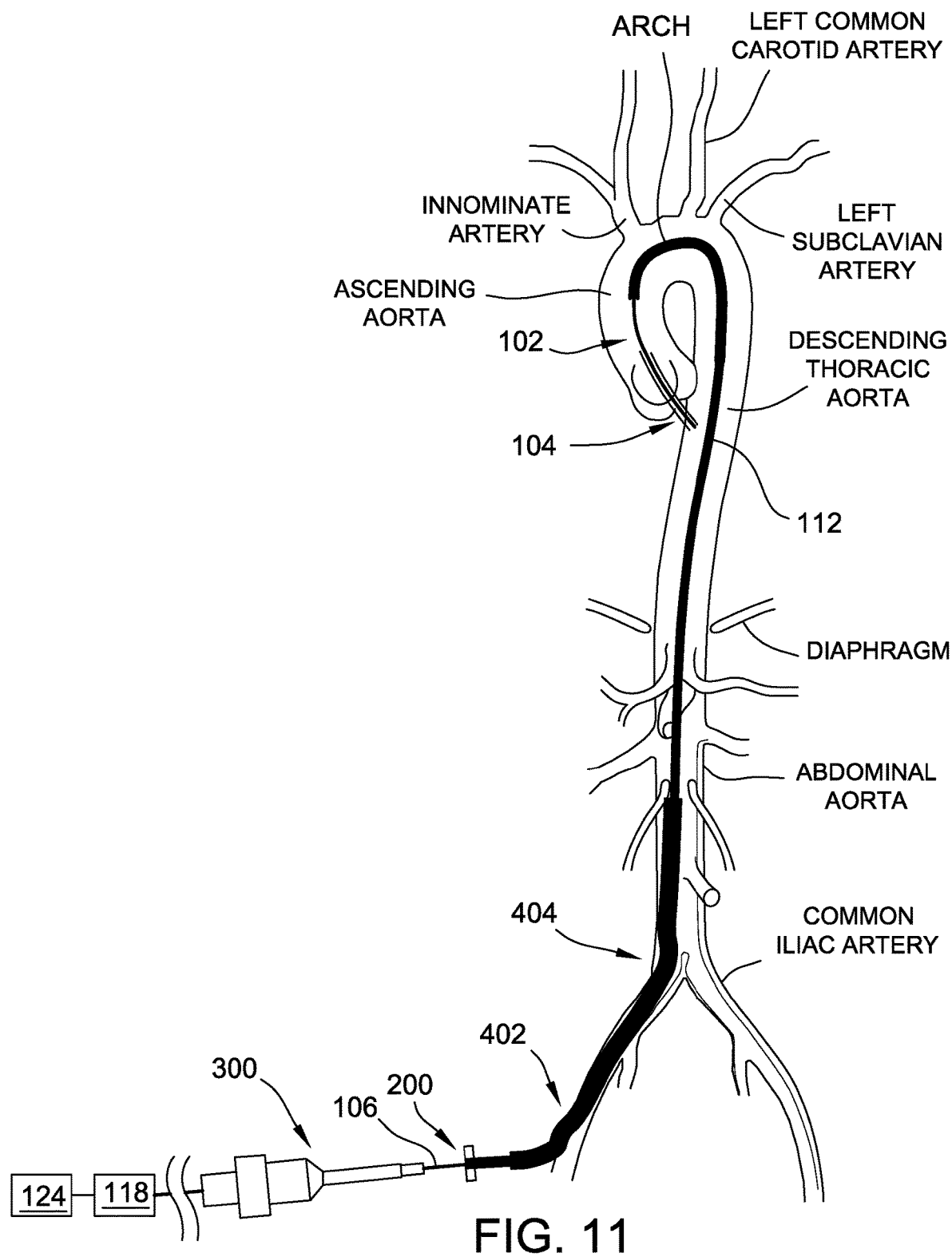
FIGS. 11-16 are simplified diagrams of a patient's vasculature illustrating various techniques for introducing and removing the catheter system of FIG. 4.

FIG. 11 is a simplified diagram of a patient's vasculature illustrating one technique for introducing the catheter system 100 of FIG. 4 into the patient's vasculature. The catheter system 100 is shown in FIG. 11 in one operational configuration, following insertion of the catheter 102 into the patient's vasculature through an incision site 402 using an introducer sheath 404.

More specifically, FIG. 11 shows the outer sheath 112 in a proximal position, with the expandable medical device 104 advanced distally out of the outer sheath 112 and in the expanded state. In some embodiments, the expandable medical device 104 is delivered to a target site by advancing the expandable medical device 104 through the patient's vasculature while the expandable medical device 104 is maintained in a collapsed state within the outer sheath 112, specifically, within the retention section 132. The expandable medical device 104 can subsequently be deployed within the patient, such that the expandable medical device 104 radially expands from the collapsed state to an expanded state, by advancing the expandable medical device 104 distally out of the outer sheath 112, as illustrated in FIG. 11.

Figure 12:
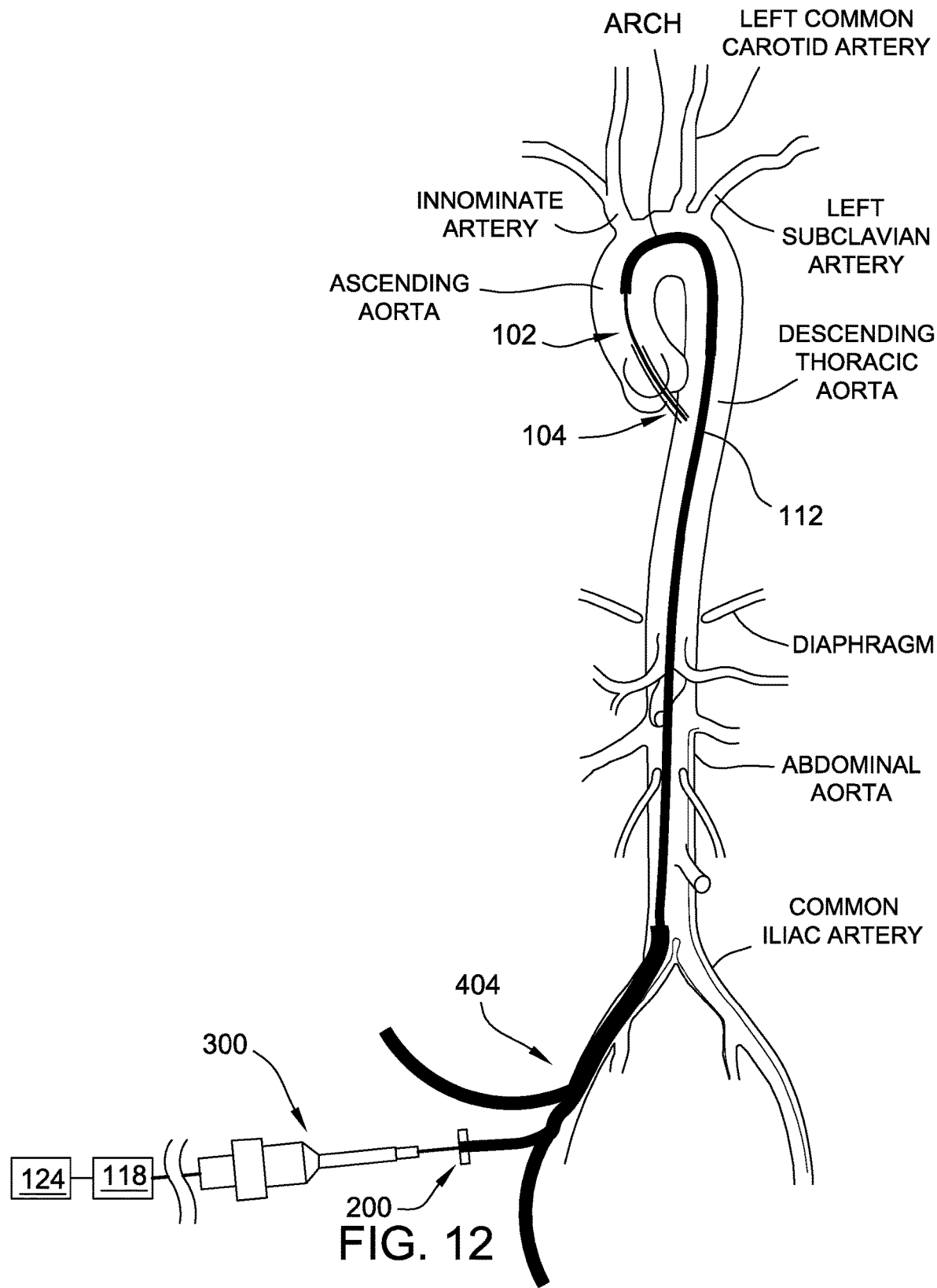

In FIG. 11, the catheter system 100 is illustrated with the introducer sheath 404 positioned within the patient's vasculature. As described herein, the recovery sheath assemblies of the present disclosure enable the introducer sheath 404 to be removed from the patient's vasculature, and thereby facilitate reducing obstructions to blood flow within the patient's vasculature. In some embodiments, for example, the recovery sheath assembly 300 is disposed on a proximal section of the catheter 102, as shown in FIG. 11. Once the distal end of the catheter 102 is advanced to a desired location within the patient, the introducer sheath 404 is removed from the patient's vasculature, and removed from the catheter 102, for example, by separating the introducer sheath 404 along a separation zone (e.g., by peeling), as illustrated in FIG. 12.

Figure 13:
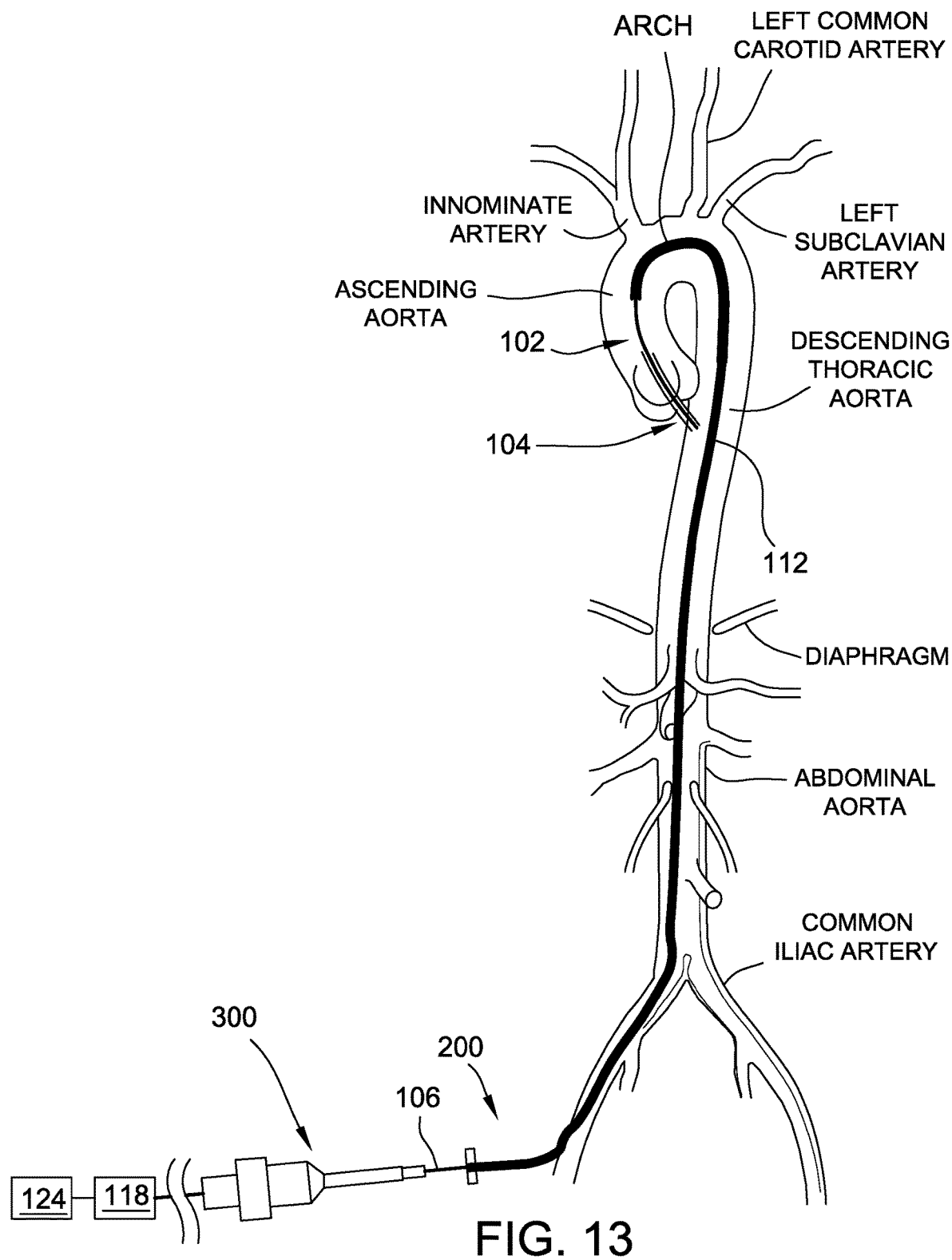
Figure 14:
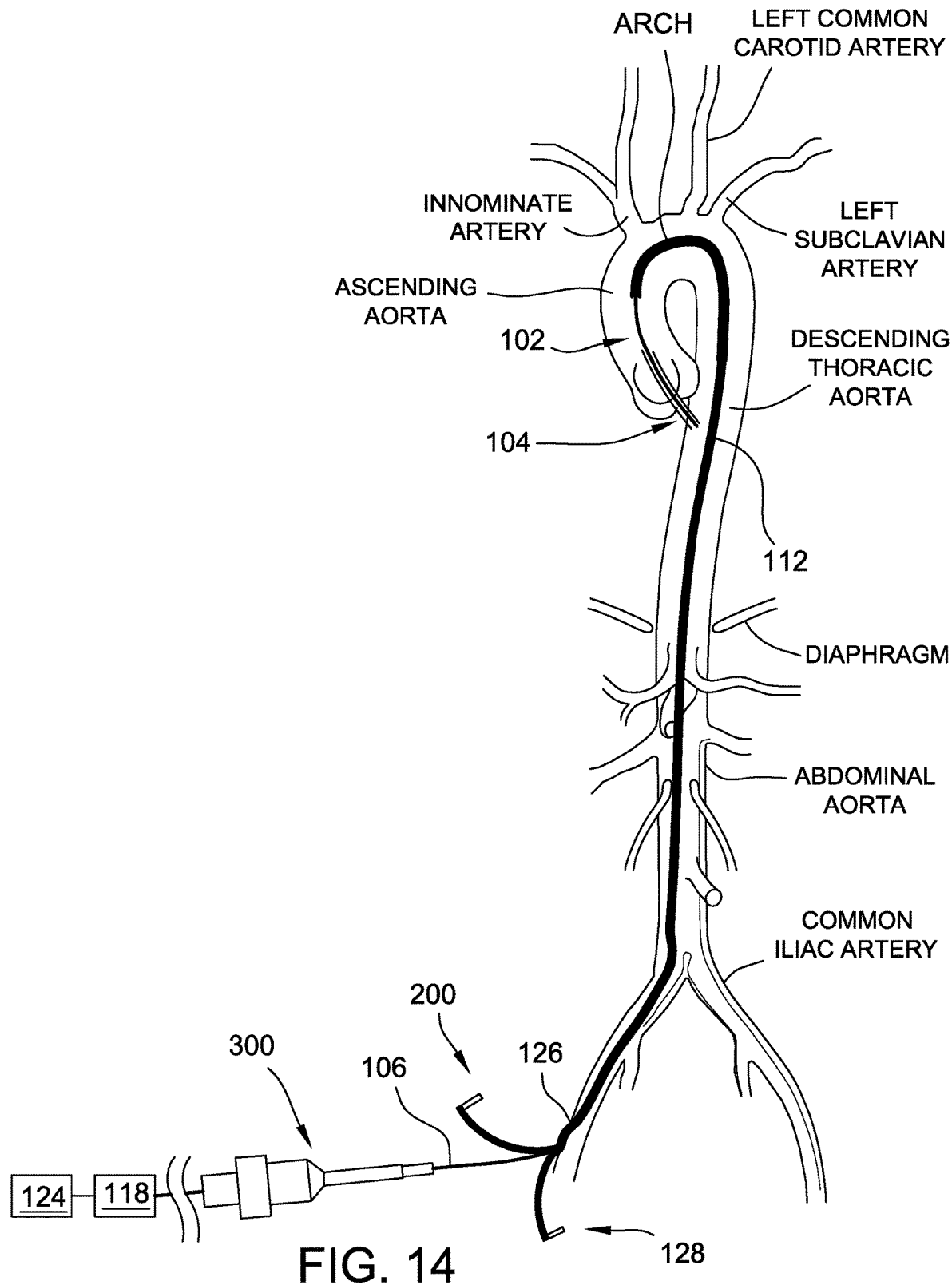

FIG. 13 illustrates the catheter system 100 of FIG. 4 in the patient's vasculature after removal of the introducer sheath 404. As shown in FIG. 13, removal of the introducer sheath 404 reduces the profile or cross-sectional area of the portion of the catheter system 100 that remains in the body, and opens up space in the vasculature for blood flow around the remainder of the catheter system 100. In accordance with the present disclosure, the profile or cross-sectional area of the catheter system 100 can be further reduced by removing the outer sheath assembly 200 from the catheter system 100. As illustrated in FIG. 14, for example, the outer sheath assembly 200 can be removed from the catheter body 106, for example, by separating the outer sheath body 126 along one or more separation zones (e.g., separation zone 202, shown in FIG. 4) such that the catheter body 106 can pass through the separation zone 202. In the illustrated embodiment, the outer sheath body 126 is separated into two segments along 126a, 126b along first and second lateral separation zones 202a, 202b (shown in FIGS. 5 and 6) by applying laterally opposing forces at the proximal end 128 of the outer sheath body 126. As the separation zones advance distally along the length of the outer sheath body 126, the outer sheath assembly 200 is pulled proximally along the catheter body 106 and out of the patient's vasculature until the outer sheath body 126 is completely removed from the patient's vasculature.

Figure 15:
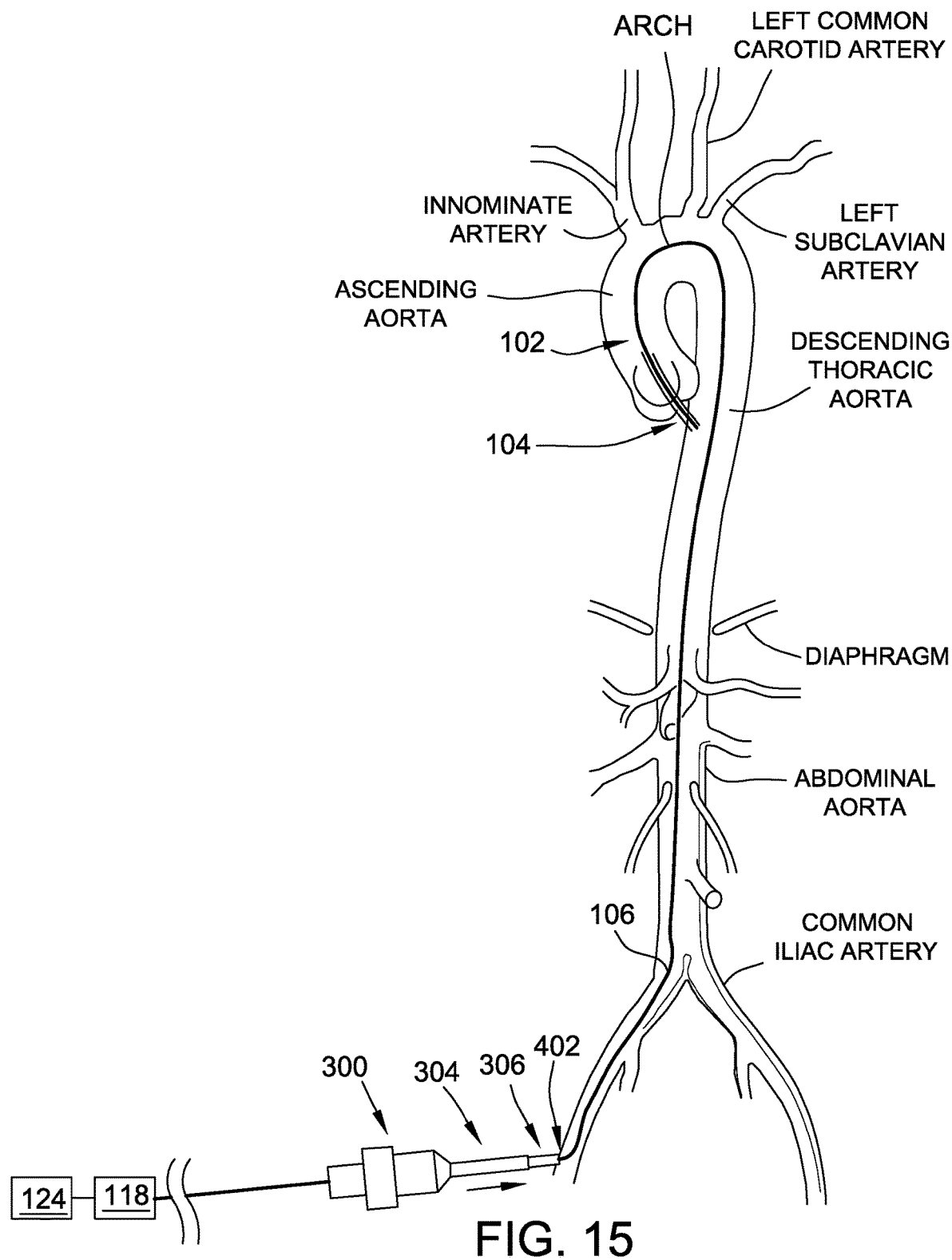

As shown in FIG. 15, removal of the outer sheath assembly 200 further reduces the profile or cross-sectional area of the portion of the catheter system 100 that remains in the body, and opens up additional space in the vasculature for blood flow around the remainder of the catheter system 100. In particular, after removal of the outer sheath assembly 200, only the reduced-diameter proximal section 134 of the catheter body 106 (shown in FIG. 1), and components enclosed therein, remains in the femoral artery. As noted above, the reduced-diameter proximal section 134 of the catheter body 106 has a diameter less than the outer diameter of the outer sheath assembly 200, and can be in the range of, for example, 7-11 Fr.

As further illustrated in FIG. 15, the recovery sheath assembly 300, including the recovery sheath 304 and the removable plug 306, can be advanced distally along the catheter body 106, subsequent to the outer sheath assembly 200 being removed from the catheter body 106, to seal the incision site 402 and/or to facilitate removal of the expandable medical device 104. More specifically, in illustrated embodiment, the recovery sheath 304 and the removable plug 306 are advanced distally along the catheter body 106, subsequent to the outer sheath assembly 200 being removed from the catheter body 106, so that the distal end 352 of the removable plug 306 (shown in FIG. 9) is positioned within the incision site 402 of the patient's vasculature. As noted above, the distal end 352 of the removable plug 306 is tapered, and can be inserted through the incision site 402 as far as needed to seal or occlude the incision site 402. Although not illustrated in FIG. 15, in some embodiments, the recovery sheath assembly 300 is advanced distally until the recovery sheath 304 is positioned within the incision site 402 to seal the incision site 402. The removable plug 306 occludes the gap formed between the relatively-large diameter recovery sheath 304 and the relatively-small diameter catheter body 106.

In other embodiments, the incision site 402 may be sealed by means other than the removable plug 306. In some embodiments, for example, the incision site 402 may be sealed by suturing around the catheter body 106 and/or by using a suture-mediated closure system, such as Perclose ProGlide™, commercially available from Abbott Laboratories. In such embodiments, the recovery sheath 304 may remain outside the patient's vasculature until just prior to removal of the catheter 102 from the patient's vasculature.

Figure 16:
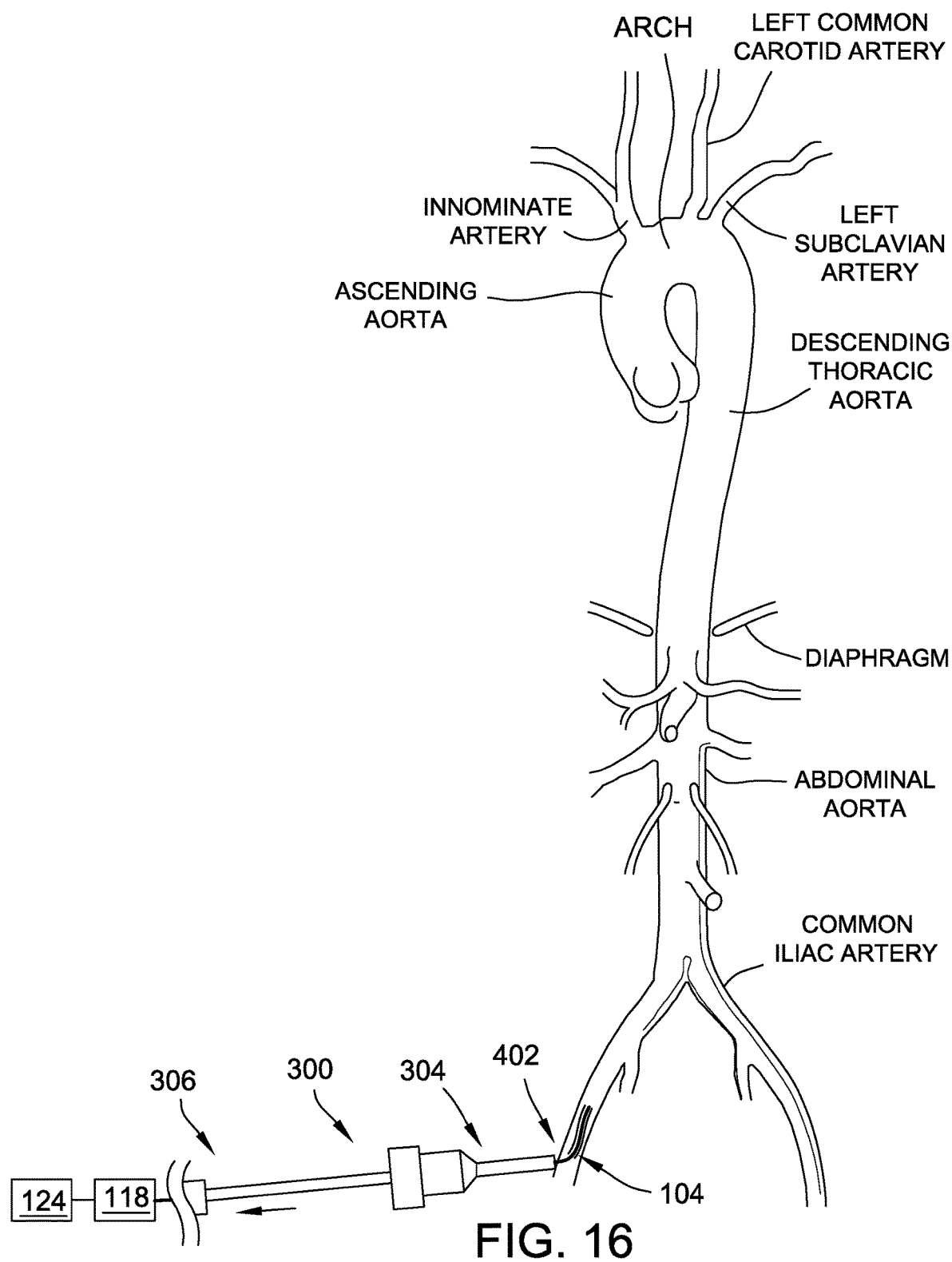

FIG. 16 illustrates one technique for removing the catheter system 100 from the patient's vasculature. In this embodiment, the catheter 102 is removed from the vasculature of the patient by pulling the catheter 102 proximally out of patient's vasculature through the recovery sheath lumen 340 (shown in FIG. 10). More specifically, the removable plug 306 is removed from the recovery sheath 304 (e.g., by sliding the removable plug 306 proximally along the catheter 102 relative to the recovery sheath 304) such that the large diameter distal end of the catheter 102 can pass through the recovery sheath lumen 340. As the catheter 102 is pulled proximally out of the patient's vasculature, as illustrated in FIG. 16, the expandable medical device 104 engages the distal end 338 of the recovery sheath 304 (shown in FIG. 9), causing the expandable medical device 104 to collapse into the collapsed configuration. The expandable medical device 104 can then be pulled proximally through the recovery sheath lumen 340, and the catheter 102 can be removed from the patient's vasculature.

Once the catheter 102 is removed from the recovery sheath 304, the valve 302 (shown in FIG. 9) may be actuated to close valve member 312 (e.g., by rotating the actuator 310 and causing the valve member 312 to compress the recovery sheath 304) to inhibit blood flow out of the recovery sheath 304. Additionally, in some embodiments, the recovery sheath 304 may be left in place, for example, to allow access for other catheters to be introduced by an operator.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A catheter system comprising:
a catheter comprising an elongate catheter body having an expandable medical device coupled with a distal end thereof;
an introducer sheath disposed over the elongate catheter body, the introducer sheath including a proximal end, a distal end, and an elongate outer sheath body extending therebetween, the introducer sheath including at least a first portion sized and shaped to receive the medical device and maintain the medical device in a collapsed state to facilitate advancing the expandable medical device through a patient's vasculature, the outer sheath body being separable from the elongate catheter body in order to eliminate an obstruction of blood flow in the patient's vasculature otherwise caused by a presence of the elongate outer sheath body of the introducer sheath; and
a recovery sheath disposed around a proximal section of the elongate catheter body, wherein the recovery sheath is sized and shaped to receive the medical device, and wherein the recovery sheath is axially movable relative to the elongate catheter body in the patient's vasculature after the introducer sheath is separated from the elongate catheter body.

2. The catheter system of claim 1, wherein the elongate outer sheath body comprises at least one longitudinally-extending separation zone, and wherein the elongate outer sheath body is separable along the at least one longitudinally-extending separation zone to enable the introducer sheath to be removed from the elongate catheter body.

3. The catheter system of claim 2, wherein the at least one longitudinally-extending separation zone extends from the proximal end of the introducer sheath to the distal end of the introducer sheath.

4. The catheter system of claim 1, wherein the elongate outer sheath body comprises at least one seam, the elongate outer sheath body configured to separate along the at least one seam, such that the elongate outer sheath body is removable from the elongate cat heter body.

5. The catheter system of claim 4, wherein the elongate outer sheath body is further configured to separate from a proximal end of the at least one seam toward a distal end of the at least one seam as the elongate outer sheath body is withdrawn from the patient's vasculature.

6. The catheter system of claim 1, wherein the introducer sheath further comprises a first handle and a second handle disposed at the proximal end, wherein the first handle and the second handle are configured to induce separation of the elongate outer sheath body along a separation zone in response to application of laterally opposing forces to the first and second handles.

7. The catheter system of claim 1, wherein the introducer sheath includes a first separation zone and a second separation zone positioned dia metrically opposite the first separation zone, and wherein the first separation zone and the second separation zone enable separation of the elongate outer sheath body into a first portion and a second portion.

8. The catheter system of claim 1, wherein a proximal portion of the elongate catheter body has an outer diameter between 8 Fr and 10 Fr, and wherein the proximal end of the introducer sheath has an outer diameter between 10 Fr and 12 Fr.

9. The catheter system of claim 1, wherein the recovery sheath includes an outer diameter and an inner diameter, the inner diameter defining a recovery s heath lumen for receiving the expandable medical device, and wherein the outer diameter is substantially the same as an outer diameter of the introducer sheath, whereby the recovery sheath is configured to seal an incision site previously occupied by the introducer sheath following insertion of the expandable medical device.

10. A method for removing an outer sheath from a catheter in situ, the method comprising:
positioning a catheter system within a blood flow lumen of a patient, the catheter system including at least:
an elongate catheter body;
a medical device coupled with a distal end of the elongate catheter body;
an introducer sheath surrounding at least a portion of the elongate catheter body; and
a recovery sheath disposed around a proximal section of the elongate catheter body, wherein the recovery sheath is sized and shaped to receive the medical device;
separating and entirely removing the introducer sheath from the elongate catheter body while the elongate catheter body is positioned within the blood flow lumen of the patient, whereby, as a result, a diameter of the catheter system is reduced in situ to reduce a physical stress on the blood flow lumen of the patient otherwise caused by a presence of the introducer sheath; and
translating the recovery sheath axially relative to the elongate catheter body to seal an incision site.

11. The method of claim 10, wherein the introducer sheath comprises at least one longitudinally-extending separation zone, and wherein the introducer sheath is separable along the longitudinally-extending separation zone, the method further comprising separating the introducer sheath from the elongate catheter body along the longitudinally-extending separation zone.

12. The method of claim 10, further comprising withdrawing the introducer sheath proximally during separation of the outer sheath, whereby the introducer sheath separates from the elongate catheter body from a proximal end of the introducer sheath toward a distal end of the introducer sheath.

13. The method of claim 10, wherein the introducer sheath comprises at least one seam, the method further comprising separating the introducer sheath from the elongate catheter body along the seam.

14. The method of claim 13, further comprising separating the introducer sheath from a proximal end of the seam toward a distal end of the seam as the introducer sheath is withdrawn from the blood flow lumen of the patient.

15. The method of claim 10, wherein the introducer sheath assembly further comprises a first handle and a second handle disposed at a proximal end of the introducer sheath, the method further comprising applying a first force to the first handle and a second force to the second handle to induce separation of the introducer sheath from the elongate catheter body.

16. The method of claim 10, wherein the introducer sheath includes a first separation zone and a second separation zone positioned diametrically opposite the first separation zone, the method further comprising separating the introducer sheath from the elongate catheter body along the first separation zone and the second separation zone.

17. The method of claim 16, wherein separating the introducer sheath from the elongate catheter body along the first separation zone and the second separation zone further comprises separating the introducer sheath into a first portion and a second portion.

18. A catheter system comprising:
a catheter comprising an elongate catheter body;
an expandable medical device;
an introducer sheath maintaining the expandable medical device in a collapsed state to facilitate advancing the expandable medical device through a patient's vasculature, the introducer sheath including:
a proximal end;
a distal end; and
an outer sheath body extending between the proximal end and the distal end, the outer sheath body including at least one longitudinally extending separation zone that defines a first outer sheath portion and a second outer sheath portion;
a first handle coupled with the first outer sheath portion at a proximal end of the first outer sheath portion; and
a second handle coupled with the second outer sheath portion at a proximal end of the second outer sheath portion
wherein the first outer sheath portion and the second outer sheath portion are removable via applied force on the first and second handles in order to remove an obstruction of blood flow in the patient's vasculature otherwise caused by the first outer sheath portion and the second outer sheath portion of the introducer sheath; and
a recovery sheath disposed around a proximal section of the elongate catheter body, wherein the recovery sheath is sized and shaped to receive the expandable medical device, and wherein the recovery sheath is axially movable relative to the elongate catheter body in the patient's vasculature after the introducer sheath is separated from the elongate catheter body.

* * * * *